United States Patent [19]
Krumdieck

[11] Patent Number: 5,148,729
[45] Date of Patent: Sep. 22, 1992

[54] BIOLOGICAL TISSUE SLICER

[76] Inventor: Carlos Krumdieck, 3408 Wellford Cir., Birmingham, Ala. 35236

[21] Appl. No.: 597,066

[22] Filed: Oct. 15, 1990

[51] Int. Cl.$^5$ ............................ G01N 1/06; B26D 1/10
[52] U.S. Cl. ...................................... 83/411.1; 83/698; 83/411.4; 83/468.7; 83/915.5
[58] Field of Search .................. 83/703, 597, 607, 608, 83/915.5, 411.1, 411.4, 468.7, 467.1, 698

[56] References Cited

U.S. PATENT DOCUMENTS 2,643,579  6/1953  Jacoby, Jr. .......................... 83/915.5
4,271,740  6/1981  Yamazaki et al. ................. 83/915.5

OTHER PUBLICATIONS

Krumdieck, Carlos L., José Ernesto DosSantos, Kung-Jey Ho, "A New Instrument for Rapid Preparation of Tissue Slices", Analytical Biochemistry, 104, 118-123 (1980).

Krumdieck Tissue Slicer Operating Instruction Manual, Publication date and publisher unknown.

"Current Techniques—Tissue Slicing and Culturing Revisited", Trends in Pharmacology Science, 8; 11-15 (1987).

Primary Examiner—Hien H. Phan
Attorney, Agent, or Firm—Jennings, Carter, Thompson & Veal

[57] ABSTRACT

A biological tissue slicer having improvements therein which enable an inexperienced operator to rapidly prepare minimally traumatized tissue slices of excellent viability and of very uniform shape and dimension. The improvements limit contact of the cutting edge of the blade with the tissue to avoid irregular surfaces and trauma to the tissue sample. The device utilizes two pins and one or more magnets to hold the blade to a rapidly reciprocally moving blade holder such that uniform tissue slices of defined dimensions are produced by eliminating excessive lateral and vertical movement of the blade.

1 Claim, 3 Drawing Sheets

BIOLOGICAL TISSUE SLICER

FIELD OF THE INVENTION

A biological tissue slicer designed to produce aseptic, thin slices of live tissue suitable for biochemical, pharmacological or toxicological studies. The present invention produces uniform tissue slices of a defined thickness with minimal damage at the cut surfaces. The slicer operates submerged in tissue culture media or in a buffered fluid. Further, the present invention relates to improvements comprising magnetically holding a blade for slicing tissue samples to a blade holder, aligning and guarding the blade to reduce exposure of the tissue sample to the cutting surface of the blade.

BACKGROUND OF THE INVENTION

Tissue culture methodologies allow physiological reactions and occurrences to be studied outside the organism without the influence of other biological reactions.

The incubation of tissue slices for short periods (hours) was introduced for biomedical studies in 1923 by Warburg. Prolonged incubations (days/weeks) were, in practice, not possible until the fifties, following the introduction of antibacterial and antifungal antibiotics.

For any tissue culture methodology to achieve maximum usefulness as a research tool, there must be uniformity between each individual tissue sample which yields uniformity and reproducibility between each separate experiment. However, in the past the production of homogeneous tissue slices from fresh tissue samples has been difficult and very dependent on the skill and experience of the technician. Past attempts to produce tissue samples which are uniform in dimension has been met with a host of problems including irreproducibility of slice thickness, contamination of tissue samples and irregular, nonreproducible trauma to the tissue adjacent to the cutting surfaces. In particular, no tissue slicer of the past has been designed to operate aseptically. In addition, a mechanical method of attachment of the blade to the blade holder which necessitated frequent tightening of the screws or clamps holding the blade in position was utilized. Consequently, the tissue sample became contaminated and inconsistencies in the geometry of the slices and irregular damage to the surfaces resulted from vertical movement of the blade. Also, in the past, tissue slicers have not limited the exposure of the uncut sample surface of the tissue sample to the blade. This unlimited exposure of the tissue sample to the blade resulted in unnecessary and harmful contact of the sample surface with the blade. Because of the above problems many investigators have not turned to tissue culture methodology. This has resulted in under utilization of a technique which is less expensive, reduces the number of experimental animals used, and with which experiments can be performed using human biopsy tissue samples, surgical resection or organ donation samples, with results that avoid the need for questionable extrapolation of results from animals to humans.

My invention enables an inexperienced technician to prepare, rapidly, tissue slices of nearly identical dimensions in an aseptic environment of defined composition and temperature while minimizing tissue trauma. The present invention accomplishes the above by holding the blade in the blade holder by a combination of two pins to limit the lateral displacement of the blade and one or more permanent magnets which provide a constant downward pull on the blade and the blade holder without impeding the reciprocation of the latter. This design eliminates the need for readjustment or tightening during use; therefore, opportunities for contamination are decreased, reproducibility of dimensions is increased and trauma to the tissue resulting from vertical "chatter" of the blade is decreased. Further, the present invention guards the blade to limit the exposure of the tissue sample to the blade to decrease the extent of trauma to the cut surfaces of the slices.

SUMMARY OF THE INVENTION

It is the object of the present invention to provide a mechanical tissue slicer which produces, rapidly, aseptic slices of live tissues of nearly identical dimensions while minimizing trauma and contamination to the tissue.

It is another object of the present invention to provide an improved method of securing a blade to a blade holder in a tissue slicing apparatus to increase reproducibility of tissue uniformity by decreasing unnecessary movement.

Yet another object of the present invention is to provide an improved method of guarding the cutting edge of the blade to minimize tissue trauma.

These and other objects and advantages of the invention will be more fully set forth in the following specification and claims considered in connection with the attached drawings to which they relate.

BRIEF DESCRIPTION OF THE DRAWINGS

Apparatus embodying features of my invention are depicted in the accompanying drawings which form a portion of this disclosure and wherein.

DESCRIPTION OF THE PREFERRED EMBODIMENT

Figure 1:
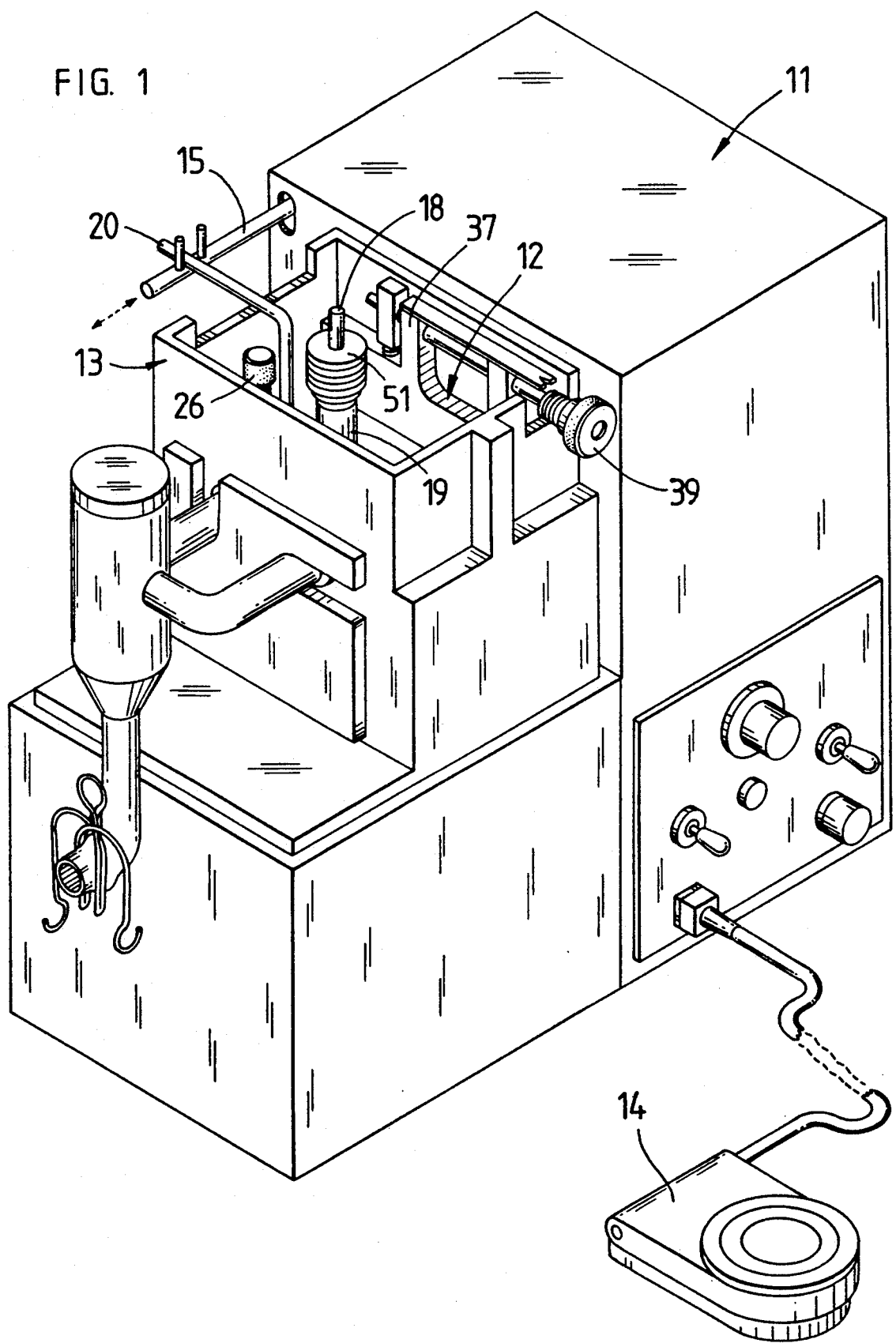
FIG. 1 shows a perspective view of the tissue slicer.
Figure 2:
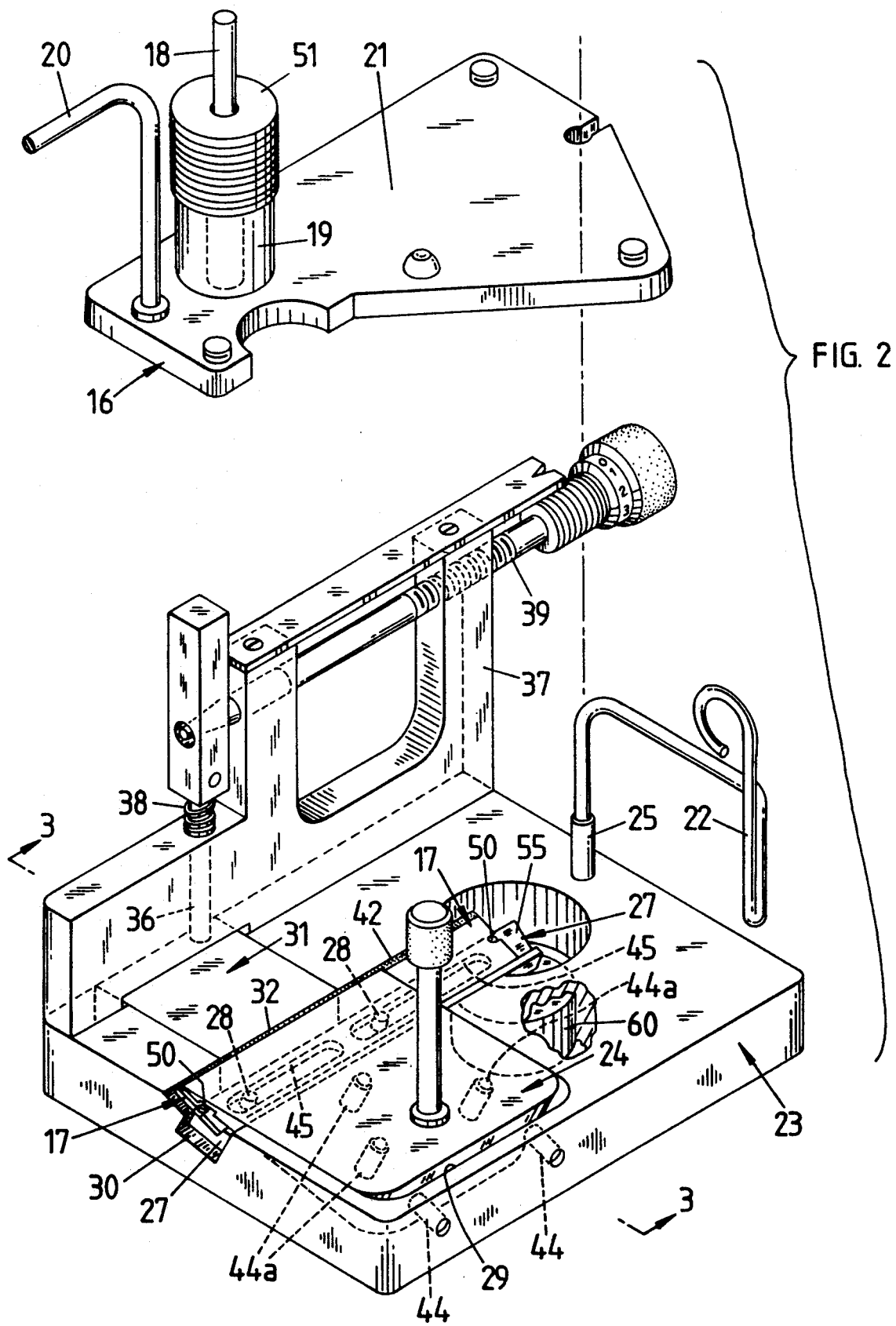
FIG. 2 is an exploded perspective view of the microtome.
Figure 3:
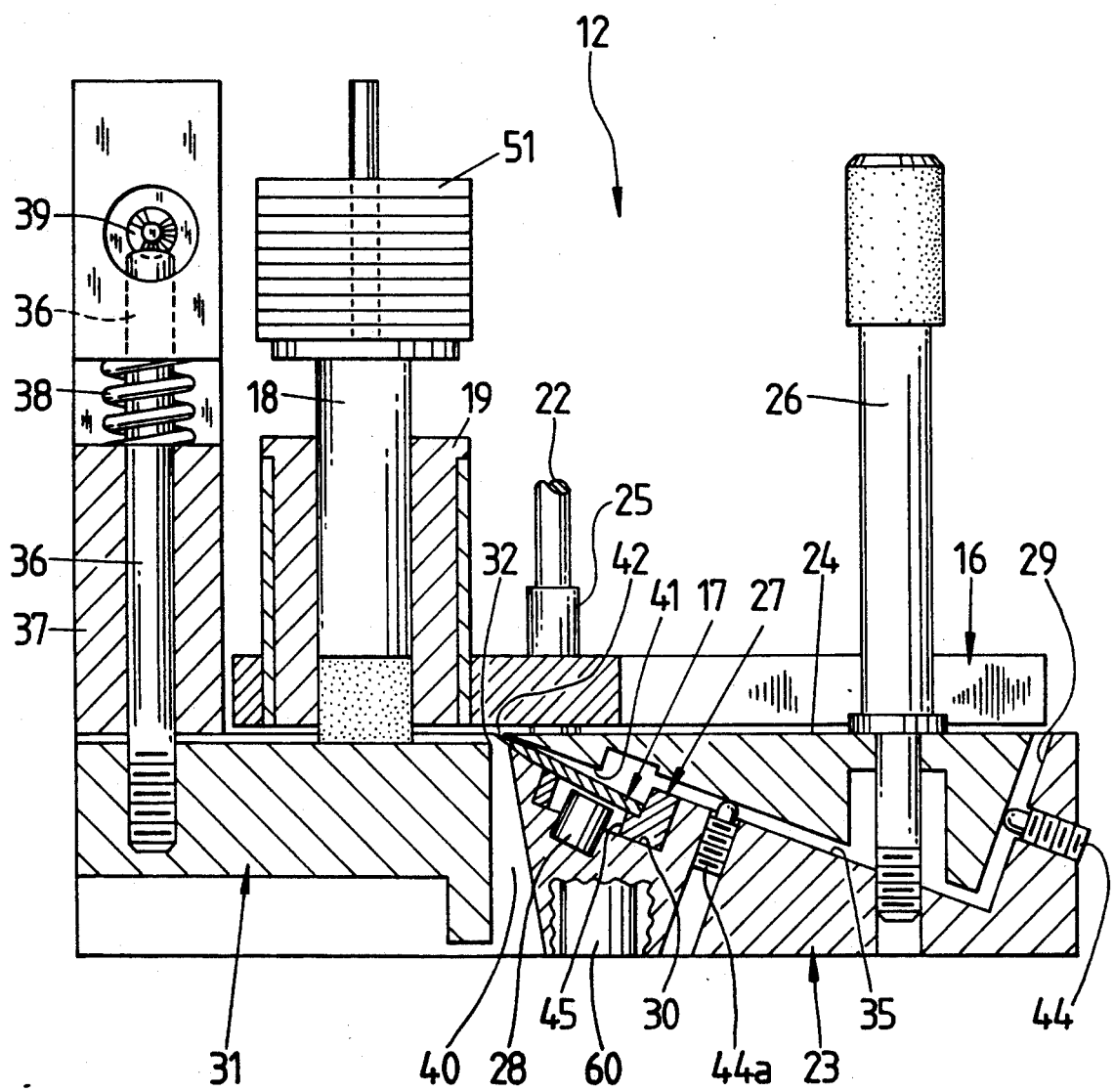
FIG. 3 is a sectional view taken along line 3—3 of FIG. 2.

A tissue slicer as shown in FIG. 1 consists of three main parts: the housing or body 11, the microtome 12, which is more clearly illustrated in FIGS. 2 and 3, and the buffer reservoir with the slice trap 13. The housing 11 contains the motors and controlling electronic circuits needed for the operation of the apparatus. As FIG. 1 illustrates, a foot pedal 14 can be used when operating under sterile conditions. The use of a foot pedal 14 allows the operator to maintain sterility of his/her gloved hands. The microtome 12 and the buffer reservoir with the slice trap 13 are autoclavable to permit the preparation of sterile slices for prolonged organ culture.

Two motors, not shown, operate separately, but in conjunction with one another to provide motion to the various components. The first motor 60 drives a rapidly reciprocating blade holder 27 and associated disposable microtome blade 17 and powers a small centrifugal pump that establishes a stream of buffer fluid to gently carry the freshly cut slices to the slice trap located outside the buffer reservoir 13. A second motor having speed control moves a reciprocating arm 15 which engages a lever arm 20 affixed to a tissue holding arm 16, as depicted in FIG. 2, to urge the tissue holding arm 16 about a pivot point defined by a post 25 which extends upwardly from a base 23. The speed control motor can be operated to slice one slice at a time or one slice after another without interruption.

The tissue holding arm 16 includes a weighted plunger 18 which is received in a tissue well 19 which is affixed to the plate 21 of the tissue holding arm 16 having a slot formed in one end thereof for engaging post 25. A spring loaded clip 22 pivotally mounted in post 25 is movable toward the side of the microtome to allow removal of the tissue holding arm 16 by lifting it vertically from the base 23.

With reference to FIG. 2, the base 23 has a slicer wedge cavity 29 formed therein to receive the slicer wedge 24 and align the top surface of the wedge with the top surface of the base 23 as shown in FIGS. 2 and 3. The cavity 29 has a first inclined surface 35 having a rectangular groove 30 formed therein for receiving the blade holder 27. The base 23 has a downwardly opening channel 40 extending therethrough adjacent the upper edge of surface 35. Supported on the base 23 adjacent channel 40 is a vertically movable slicer plate 31 having a reference edge 32. Mounted within rectangular groove 30 are one or more permanent magnets 28 preferably disposed along the longitudinal axis of the groove 30. Blade holder 27 is slidingly received within the groove 30 and has one or more longitudinal slots 45 formed therein which allow the blade holder to move longitudinally about the magnets 28. Formed in the upper surface of the blade holder 27 is a receiving surface 55 on which the blade 17 rests. Pins 50 extend upwardly from the blade holder 27 to prevent relative longitudinal motion between the blade 17 and blade holder 27. Receiving surface 55 holds the blade at a preferred angle such that the blade extends upwardly over channel 40 and proximal reference edge 32.

The receiving surface 55 of the blade holder 27 positions the blade 17 such that the top beveled surface forming the cutting edge of the blade 17 is overlaid by the undersurface 41 of the slicer wedge 24. Thus, the blade 17 is offset at an angle of approximately 7° from the inclined surface 35 of the triangular prismatic cavity 29. While the 7° offset is not a numerical absolute, it should be offset to allow the beveled surface of the blade 17 and the overlying undersurface 41 to extend in close parallel relationship.

Magnets 28 hold the blade securely against the receiving surface 55 of the blade holder 27 and pull the blade holder 27 within the groove 30 thereby substantially eliminating vertical movement of the blade 17 and the blade holder 27.

The wedge 24 is held within the cavity 29 by a threaded member 26 which extends through the wedge and engages the base 23. The wedge 24 is held within the cavity 29 supra-adjacent the blade holder 27 and blade 17. The upper surface of the wedge is adjusted by adjusting members 44 and 44a.

FIGS. 2 and 3 depict the mechanism which positions the slicer plate 31 at variable levels to produce a slice of a desired thickness. A back plate 37 which extends upwardly from the base 23 and carries therein horizontally disposed rotably mounted screw adjustment rod-like member 39 which rests on a rod-like member 36 vertically mounted within the back plate 37 and positioned upwardly by a spring 38. The screw adjustment rod 39 has a conical end which rests atop the rod-like member 36. Rotation of the screw adjustment rod-like member 39 varies the engagement of the conical end with the rod-like member 39 causing the rod-like member 39 to move vertically then to move the slicer plate 31. That is to say, the blade 17 remains at a predetermined height and the slicer plate 31 is moved relative to the blade 17 to vary slice thickness.

With reference to FIG. 3, the following aspects of the present invention can be more clearly understood. As shown in FIG. 3, the undersurface 41 of the slicer wedge 24 extends parallel to the bevel of the blade and overlies a portion of the beveled surface 42. This limited exposure minimizes the duration of tissue exposure to the beveled surface 42. The adjusting members 44 are adjusted to allow only about 0.3 mm of the beveled surface 42 to be exposed and in conjunction with adjusting members 44a align the upper surface of the slider wedge 24 with the slicer plate 31.

Note, the uncut tissue from the tissue sample is supported on the upper surface of the wedge while the tissue slice is carried through channel 40; thus, only minimal contact between the reciprocating blade 17 and the uncut portion of the overlying tissue sample is insured by my design.

To operate the slicer, the tissue sample is placed within the tissue well 19 then the plunger 18 is replaced atop the tissue sample. The number of washers 51 used with the plunger 18 determines the downward force applied to the tissue sample. Next, the motors are initiated which move the tissue holding arm 16 and establish the reciprocating movement of the blade 17 held within the blade holder 27 and the stream of buffer fluid necessary to quickly carry freshly cut tissue slices to the slice trap 13. As the tissue sample in the tissue well 19 affixed to the tissue holding arm 16 moves across the reciprocating blade 17 tissue slices of desired dimension are produced which are carried away through the channel 40 to the buffer reservoir and slice trap 13 by the buffer stream. The second motor which drives the tissue holding arm 16 can be either preset to produce slices continuously or to cut a single slice and stop. The speed of this motor can be varied to regulate the rate at which a block of tissue is fed across the reciprocating blade. This allows cutting tissues of varied consistencies.

While I have shown my invention in one form, it will be obvious to one skilled in the pertinent art that it is not so limited, but is susceptible to various changes and modifications without departing from the spirit thereof.

What I claim is:

1. An improvement to a biological tissue slicer for producing uniform tissue slices of a defined thickness from a tissue sample, usable in tissue culture experiments, having a base including a slicer plate, variable in height relative to an upper surface of said base with a reference edge of said plate extending horizontally parallel to an upwardly opening cavity in said base, there being received within said cavity a substantially planar blade mounted on a driven rectangular blade holder which moves reciprocally within a rectangular groove found in said base within said cavity, the improvement comprising at least one magnet cooperatively affixed within said rectangular groove and extending within a longitudinal slot, formed in said blade holder, in spaced relation to and beneath said blade to exert an attractive force on said blade urging said blade into planar abutment with said blade holder to prevent excessive movement of said blade transversely of the plane of said blade, said blade holder supporting said blade between retaining members affixed thereto, engaging said blade to prevent relative longitudinal motion between said blade holder and said blade as said blade holder and blade concomitantly reciprocate along said rectangular groove relative to said magnet.

* * * * *